US009775612B2

(12) United States Patent
Harris

(10) Patent No.: US 9,775,612 B2
(45) Date of Patent: Oct. 3, 2017

(54) LINEAR ROTATION MECHANISM FOR HEMOSTASIS CLIP DEVICE AND OTHER DEVICES

(71) Applicant: BOSTON SCIENTIFIC SCIMED, INC., Maple Grove, MN (US)

(72) Inventor: Colby Harris, Weston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 507 days.

(21) Appl. No.: 13/728,672

(22) Filed: Dec. 27, 2012

(65) Prior Publication Data

US 2013/0172909 A1   Jul. 4, 2013

Related U.S. Application Data

(60) Provisional application No. 61/581,917, filed on Dec. 30, 2011.

(51) Int. Cl.
| | |
|---|---|
| *A61B 17/10* | (2006.01) |
| *A61B 17/128* | (2006.01) |
| *A61B 17/00* | (2006.01) |
| *A61B 17/29* | (2006.01) |

(52) U.S. Cl.
CPC .......... *A61B 17/10* (2013.01); *A61B 17/1285* (2013.01); *A61B 2017/0034* (2013.01); *A61B 2017/293* (2013.01); *A61B 2017/2905* (2013.01); *A61B 2017/2929* (2013.01)

(58) Field of Classification Search
CPC .................. A61B 17/10; A61B 17/128; A61B 2017/00371; A61B 2017/00473; A61B 2017/12004; A61B 2017/2903; A61B 2017/2913; A61B 2017/2916; A61B 2017/293; A61B 2017/2934; A61B 2017/2936; A61B 2017/2929; A61B 2017/2905; A61B 2017/0034

See application file for complete search history.

(56) References Cited

U.S. PATENT DOCUMENTS

| | | | |
|---|---|---|---|
| 4,590,936 A * | 5/1986 | Straub et al. ................ | 606/174 |
| 5,766,184 A | 6/1998 | Matsuno et al. | |
| 5,776,146 A * | 7/1998 | Sackier .............. | A61B 17/122 |
| | | | 606/142 |
| 5,893,875 A * | 4/1999 | O'Connor .............. | A61B 17/29 |
| | | | 606/167 |
| 6,027,522 A * | 2/2000 | Palmer ......................... | 606/205 |
| 6,602,262 B2 * | 8/2003 | Griego et al. ................ | 606/113 |
| 6,819,959 B1 * | 11/2004 | Doan et al. ................... | 607/127 |
| 7,722,549 B2 * | 5/2010 | Nakao ................ | A61B 10/0266 |
| | | | 600/564 |
| 7,862,553 B2 * | 1/2011 | Ewaschuk .............. | A61B 17/29 |
| | | | 604/264 |
| 2010/0042141 A1 | 2/2010 | Messerly et al. | |

* cited by examiner

*Primary Examiner* — Sarah W Aleman
(74) *Attorney, Agent, or Firm* — Fay Kaplun & Marcin, LLP

(57) ABSTRACT

A medical device includes a handle, a flexible member extending from a proximal end connected to the handle to a distal end, a rotation mechanism connected to the distal end of the flexible member, an end effector coupled to a distal portion of the rotation mechanism and a push member extending through the handle and flexible member and connecting to the rotation mechanism, the rotation mechanism being configured and dimensioned to convert axial movement of the push member into rotation of the end effector.

18 Claims, 3 Drawing Sheets

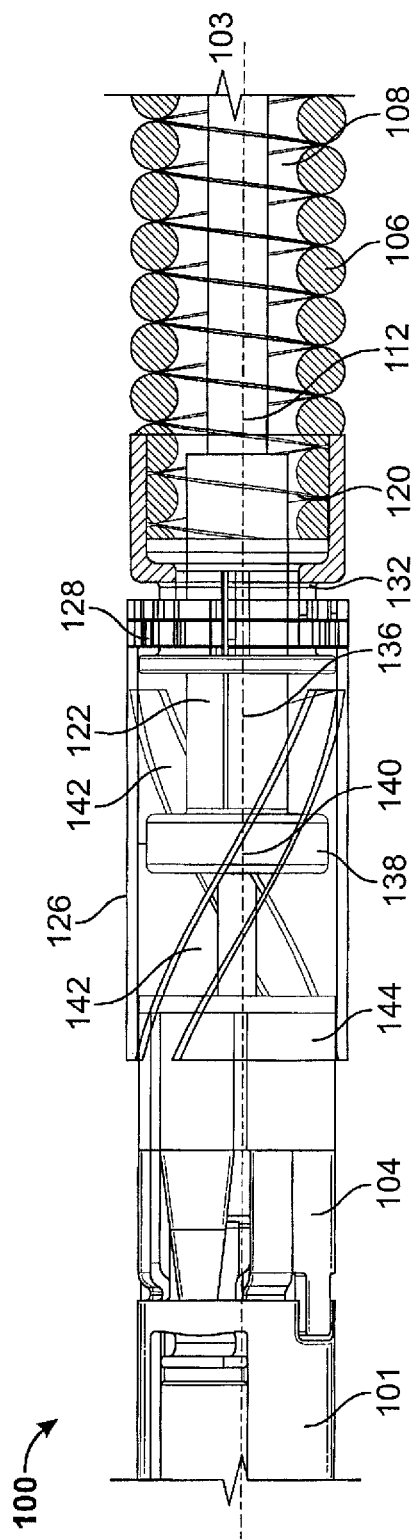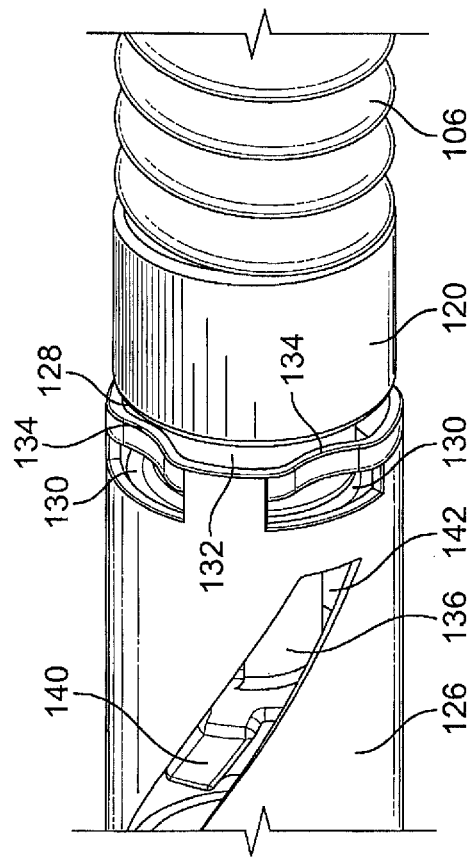

LINEAR ROTATION MECHANISM FOR HEMOSTASIS CLIP DEVICE AND OTHER DEVICES

PRIORITY CLAIM

This application claims the priority to the U.S. Provisional Application Ser. No. 61/581,917, entitled "Linear Rotation Mechanism For Hemostasis Clip Device And Other Devices" filed on Dec. 30, 2011. The specification of the above-identified application is incorporated herewith by reference.

BACKGROUND

Pathologies of the gastro-intestinal ("GI") system, the biliary tree, the vascular system and other body lumens are commonly treated through endoscopic procedures, some of which require active and/or prophylactic hemostasis to control internal bleeding. Specialized endoscopic devices are used to deliver the hemostasis devices (e.g., clips) to desired locations within the body and to position and deploy the hemostasis devices at the desired locations. Manipulation of the hemostasis device about a portion of target tissue is often difficult and may require extensive effort including attempts to rotate the hemostasis device relative to the target tissue to achieve proper positioning of the clip to ensure adequate sealing of a wound or other opening in tissue. However, when such a long flexible device is rotated, they tend to wind-up making it difficult or impossible to effectively transmit rotation to the hemostasis devices in a controlled manner.

SUMMARY OF THE INVENTION

The present invention is directed to a medical device comprising a handle, a flexible member extending from a proximal end connected to the handle to a distal end, a rotation mechanism connected to the distal end of the flexible member, an end effector coupled to a distal portion of the rotation mechanism and a push tube extending through the handle and flexible member and connecting to the rotation mechanism, the rotation mechanism being configured and dimensioned to convert axial movement of the push tube into rotation of the end effector.

BRIEF DESCRIPTION OF THE DRAWINGS

FIG. 2 shows a second transparent view of the device of FIG. 1;

FIG. 3 shows a perspective view of a rotation mechanism of the device of FIG. 1.

DETAILED DESCRIPTION

Figure 1:
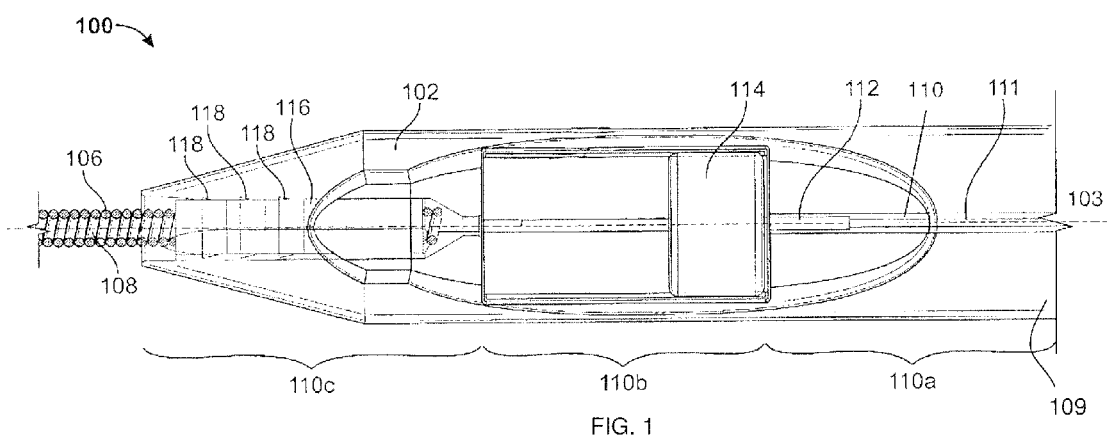
FIG. 1 shows a first transparent view of the exemplary device according to the invention.

The present invention may be further understood with reference to the following description and the appended drawings, wherein like elements are referred to with the same reference numerals. The present invention relates to a device enabling rotation of an end effector attached to a flexible endoscopic device. In one embodiment of the invention, the end effector is a device for applying one or more hemostatic clips. The exemplary device according to the invention permits rotation of the clip(s) to aid in positioning thereof relative to target tissue. Specifically, the exemplary device according to the invention is configured to rotate the clip(s) relative to an outer sheath encasing the clip(s). The rotation mechanism converts an axial force applied at a proximal actuator into a rotational force rotating the clip(s). It is noted that although the rotation mechanism disclosed herein has been described with respect to clipping devices, the rotation mechanism may also be designed to perform any of a variety of endoscopic procedures including, but not limited to, band ligation, injection therapy, thermal electro-hemostasis, fine-needle aspiration, etc. and the end effector may comprises any opening/closing instrument selected from the group comprises a clip, combination therapy needle, biopsy forceps, scissors, graspers, clamps, etc. It should be noted that the terms "proximal" and "distal," as used herein, are intended to refer to a direct toward (proximal) and away from (distal) a user of the device.

As shown in FIGS. 1-4, a device 100 according to an exemplary embodiment of the invention extends along a longitudinal axis 103 from a proximal end (not shown) including a handle 102 accessible to a physician or other user in an operative configuration to a distal end (not shown) comprising an end effector (not shown). In an operative configuration, the end effector (not shown) is inserted into a living body (e.g., through a naturally occurring bodily orifice, a percutaneous orifice, transluminal access, or the like) and advanced through the body (e.g., via a natural body lumen, a percutaneous orifice, transluminal access, or the like) to a site adjacent to target tissue. As indicated above, the end effector (not shown) according to this embodiment comprises a clip containing capsule 101 a proximal end of which is releasably attached to a bushing 104 which is coupled to a rotation mechanism, as will be described in greater detail later on. The rotation mechanism is further connected to a distal end of a flexible member 106 which is coupled to the handle 102. The flexible member 106 according to this embodiment is formed as an elongated coil with a channel 108 extending therethrough and is sized and configured for insertion through a working channel of an endoscope (i.e., with an outer diameter less than an inner diameter of the working channel).

The handle 102 includes an elongated channel 110 extending therethrough divided into first 110 a, second 110 b and third 110 c sections open to one another. The first section 110 a extends from the proximal end 109 of the handle 102 distally a predetermined distance. The first section 110 a has an outer diameter substantially equivalent to or greater than an outer diameter of a push tube 112 extending through the handle 102. Specifically, the push tube 112 extends longitudinally through the handle 102 to the channel 108 and extends distally therepast a predetermined distance to a torque gear 122, as will be described in greater detail below. A control wire 111 extends through the push tube 112 and distally therefrom to connect to an end effector (not shown). In an exemplary embodiment, the push tube 112 may be formed of one or more of Nitinol, PEEK, and any plastic material having similar mechanical properties including sufficient rigidity and flexibility. The second section 110 b extends distally from a distal end of the first channel section 110 a a predetermined distance and has an outer diameter greater than an outer diameter of the first section 110 a. In an exemplary embodiment, the outer diameter of the second section 110 b is substantially equivalent to or greater than an outer diameter of a push tube grip 114 permanently attached to an outer wall of the push tube 112. The push tube grip 114 is formed as a substantially cylindrical element immovably gripping an outer wall of the push tube 112. As those skilled in the art will understand, the push tube grip 114 may be attached to the push tube 112 by a weld, crimp, adhesive or other attachment mechanism. The push tube grip 114 is configured to be both rotatable and longitudinally movable within the second section 110 b. The push tube grip 114 maintains longitudinal alignment with the central longitudinal axis 103 by engagement with walls of the second section 110 b. In an exemplary embodiment, the second section 110 b is dimensioned so that the push tube grip 114 may move axially therewithin by approximately 19.05 mm, although any other length is also envisioned without deviating from the scope of the invention. The third section 110 c extends distally from a distal end of the second section 110 b to the distal end of the handle 102. An outer diameter of the third section 110 c is configured and dimensioned to receive a portion of the flexible member 106 therein. The third section 110 c also comprises a flared crimp band 116 having a plurality of flared protrusions 118 configured to frictionally engage walls of the third channel section 110 c. In an operative configuration, the crimp band 116 is crimped onto the flexible member 106 to permanently affix the flexible member 106 to the handle 102. It is noted, however that any other attachment mechanism may be used without deviating from the scope of the invention (e.g., welding, adhesive, etc.).

The flexible member 106 extends distally from the handle 102 by a length conforming to the requirements of a particular procedure. A distal end of the flexible member 106 is coupled to a rotational base 120 formed, for example, of Delrin or any other material with similar mechanical properties to provide a lubricious surface aiding in rotation of an end effector (not shown) coupled thereto. In one exemplary embodiment, the rotational base 120 may be coated with Teflon, silicone, graphite, melted polymer, or any other suitable biocompatible material having similar properties, as those skilled in the art will understand. The push tube 112 extends through the rotational base 120 and terminates at a torque gear 122 distal of the rotational base 120. Specifically, a distal end of the push tube 112 in this embodiment is connected to the torque gear 122 via one or more of a weld, screw thread, cross pin, crimp and an adhesive although any other attachment means may be used without deviating from the scope of the invention. As shown in FIGS. 2-3, the torque gear 122 is housed within a substantially cylindrical and hollow torque converter 126. A proximal end 128 of the torque converter comprises four slots 130 cut therein (e.g., laser-cut, stamped, etc.) and extending through a wall thereof. The proximal end 128 is positioned over a recessed groove 132 provided on a distal end of the rotational base 120 and crimped to form four crimp bands 134 with the crimp bands 134 configured to axially hold the rotational base 120 against the torque converter 126 while permitting rotation of the rotational base 120 relative thereto. It is noted that any number of sufficient crimp bands 134 is conceivable, including two, three, five, six, and so forth without deviating from the scope of the invention. The crimp bands 134 also permit pivotal deflection of the torque converter 126 relative to the rotational base 120 by approximately 10° relative to the central longitudinal axis 103. It is noted, however, that the torque converter 126 may deflect relative to the rotational base at approximately 5-20° without deviating from the scope of the invention. In yet another embodiment, the torque converter 126 may deflect by approximately 0-20° or 0-30° to, for example, permit accommodation of an end effector (not shown) that does not pivot relative to a longitudinal axis. As those skilled in the art will understand, this deflection enhances flexibility of the device 100 aiding in insertion thereof to a target site in a body. As those skilled in the art will understand, an angularity of the torque converter may be influenced by one or both of a depth of the groove 132 and a height of the crimp bands 134. Furthermore, the crimp bands 134 may have optimized cross-sectional profiles (e.g., triangular, arched, etc.) to influence the angularity. In an alternate embodiment (not shown), the groove 123 may instead be formed as one or more protrusions including a rib extending around a perimeter of the distal end of the rotational base 120. In this embodiment, the crimp bands 134 may be formed as one or more grooves configured to receive the protrusions or rib and crimped thereover.

The torque gear 122 is formed as an elongated substantially cylindrical element having a first proximal cylindrical portion 136 with a first outer diameter. In an exemplary embodiment, the first outer diameter is smaller than an inner diameter of the rotation base 120 through which the torque gear 122 extends. The torque gear 122 also comprises a second cylindrical portion 138 having an outer diameter substantially equal to or less than the inner diameter of the torque converter 126 and larger than the inner diameter of the rotation base 120. The second cylindrical portion 138 comprises first and second wings 140 extending radially outward from opposing walls thereof. The wings 140 according to this embodiment have a substantially rectangular cross-section and are configured to engage slots 142 machined into the torque converter 126 and extending along a length thereof. However, wings 140 may be optimized for movement within slots 142, for example by having a substantially round profile. Furthermore, a contour area of each of the wings 140 may be minimized to reduce friction with the slots 142. In one embodiment, the edges of the wings 140 may be substantially rounded. The torque converter 126 comprises a pair of elongated slots 142 extending proximally from a distal end thereof in a substantially helical pattern. In an exemplary embodiment, the slots 142 extend through the torque converter 126. In another embodiment (not shown), the slots 142 may extend into a wall of the torque converter 126 by a limited depth configured to engage the wings. In yet another embodiment, only one slot 142 may be provided. Although the exemplary embodiment depicted in FIGS. 1-3 is described with two helical slots 142 and two wings 140, any number of wings and slots may be used without deviating from the scope of the invention. Furthermore, a length and curvature of the slots 142 may be modified to impart a desired rotation to an end effector, as will be described in greater detail below. Specifically, the slots 142 should be arranged over the torque converter 126 to minimize an amount of force required to convert axial translation into rotation, as those skilled in the art will understand.

Figure 4:
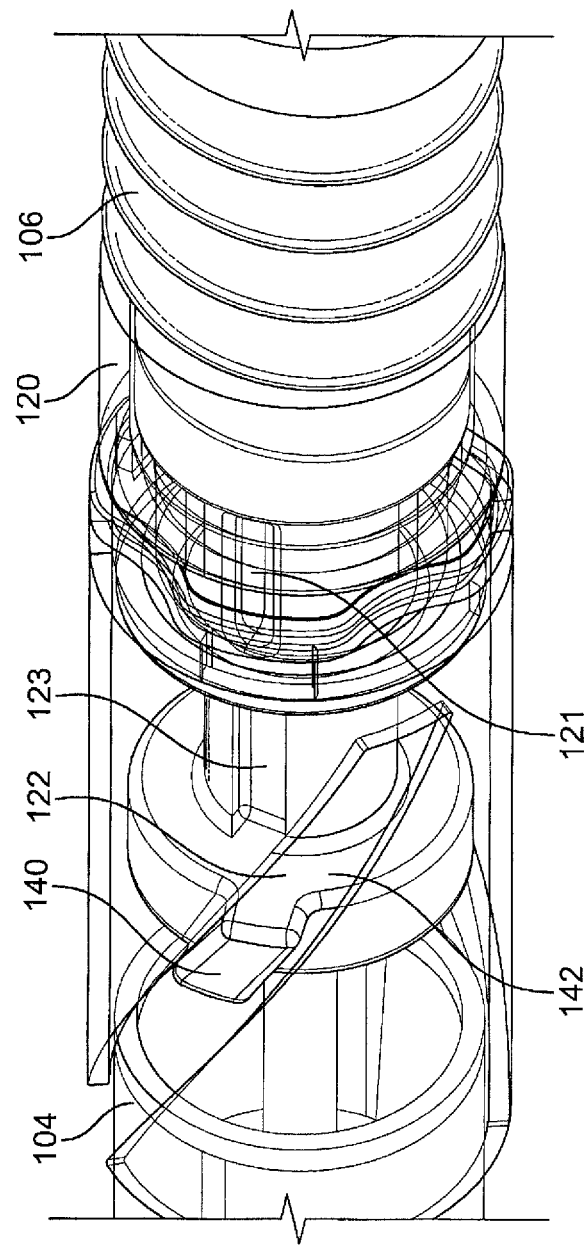
FIG. 4 shows a transparent view of the rotation mechanism of FIG. 3.

In an operative configuration, axial movement of the push tube 112 and the torque gear 122 is translated to rotation of the end effector (not shown) due to engagement of the wings 140 with the slots 142. Specifically, since the torque gear 122 is unable to rotate independently of the flexible member 106, axial movement of the push tube 112 in a distal direction causes the torque converter 126 and any components attached to a distal end thereof, to rotate. In one embodiment, a distal end 144 of the torque converter 126 is permanently attached to the bushing 104 via a weld, crimp, or other fixation method, as those skilled in the art will understand. The bushing 104 may be further connected to a capsule 101 housing a clip or other end effector which, consequently, rotates therewith. The exemplary device according to the invention permits rotation of the torque converter 126 and end effector independently of the flexible member 106 and handle 102, thus avoiding complications due to winding-up along the length of the flexible member. Specifically, as shown in FIG. 4, the rotational base 120 comprises a guide rib 121 located on an inner wall thereof and configured to mate with a guide groove 123 provided on an outer wall of the torque gear 122. This mating arrangement compels alignment between the torque gear 122 and the rotational base 120 attached to the flexible member 106 facilitating engagement of the wings 140 with the slots 142 to permit a conversion of axial movement of the push tube 112 into rotation.

In accordance with an exemplary method of the invention, an end effector is attached to the capsule 101 and the flexible member 106 is inserted through an endoscope until a distal end of the device 100 comprising the end effector (not shown) extends from the distal end of the endoscope exposed to a target portion of tissue. The device according to the invention is configured to prevent unwanted axial movement of the push tube 112 when the push tube 112 has been moved to a desired position. Specifically, the push tube 112 is configured such that a neutral axis thereof is maintained along its central longitudinal axis regardless of a curvature thereof. In contrast, the flexible member 106, which is formed of a coil, is configured such that its neutral axis deviates from a central longitudinal axis thereof when curved during insertion, permitting the flexible member 106 to adjust a length thereof to aid in insertion through tortuous anatomy. This configuration allows a length of the flexible member 106 to adjust during insertion through the body while preventing unwanted movement of the push tube 112. In another embodiment (not shown), the handle 102 may comprise a locking mechanism (not shown) configured to lock an axial position of the push tube 112 relative to the flexible member 106. The locking mechanism may be formed as a ratchet pinion, gears, ratchet, etc.

In some embodiments, the end effector (not shown) or any part of the device 100 may have an endoscopically visible marker (e.g., radiopaque, etc.) to provide visual feedback of an orientation thereof within the body. Once the end effector (not shown) has been positioned at a target location, a physician or other user moves the push tube 112 distally via an actuation mechanism (not shown) on the handle 102. In an exemplary embodiment, distal movement of the push tube grip 114 by approximately 6.35 mm within the second section 110*b* is sufficient to rotate the end effector (not shown) a complete cycle as dictated by the wings 140 and slots 142. As those skilled in the art will understand, a remaining length of the second section 110*b* is provided to permit axial movement of the push tube grip 114 therewithin when the device 100 is inserted through tortuous anatomy. Specifically, as noted above, an overall length of the flexible member 106 is changed when bent to permit insertion through tortuous anatomy. Since the push tube 112 and push tube grip 114 maintain a constant effective length, movement of the push tube grip 114 within the second section 110*b* enhances flexibility of the flexible member 106. Once the end effector has been rotated to a desired orientation relative to the target tissue, the control wire 111 extending through the device 100 is actuated to move the end effector to perform a desired operation (e.g., clip tissue, etc.) Specifically, the control wire 111 may operably move the end effector (e.g., a clip) between a closed configuration wherein first and second arms are separated from one another by a first distance and an open configuration wherein the first and second arms are separated from one another by a second distance greater than the first distance. In addition, the whole device 100 may still be rotated to provide further rotation to the end effector separately from the rotation provided by the torque converter 126.

It will be understood by those of skill in the art that individual features of the embodiments described above may be omitted and or combined to form alternate embodiments. Furthermore, it will be understood by those skilled in the art that various modifications can be made in the structure and the methodology of the present invention, without departing from the spirit or scope of the invention. For example, although the present invention has been described with respect to a clipping device, the exemplary system and method may also be used to perform biopsy procedures or any other medical procedure wherein improved rotation of a component is required in combination with a function of opening/closing a device, extending/retracting a device into tissue, etc., as those skilled in the art will understand. Furthermore, although the present invention has been described with respect to a removable capsule 101, the exemplary rotation drive mechanism according to the invention may also be used with a biopsy tool or any other medical device non-removably attached to the rotation drive mechanism. Furthermore, the torque converter 126 may be formed as a part of an end-effector in an embodiment wherein the end-effector is permanently attached to the device 100. It is therefore respectfully submitted that the exemplary rotation drive mechanism according to the invention may be employed in any other medical device requiring precise rotational control without deviating from the spirit and scope of the invention. Thus, it is intended that the present invention cover the modifications and variations of this invention provided that they come within the scope of the appended claims and their equivalents.

What is claimed is:

1. A medical device, comprising:
    a handle that remains outside a body accessible to a user;
    a flexible member extending from a proximal end connected to the handle to a distal end;
    a rotation mechanism connected to the distal end of the flexible member;
    an end effector releasably coupled to a distal portion of the rotation mechanism via a bushing; and
    a push member extending through the handle and flexible member and connecting to the rotation mechanism, the rotation mechanism being configured and dimensioned to convert axial movement of the push member into rotation of the end effector.

2. The medical device of claim 1, wherein the rotation mechanism comprises a torque gear connected to a distal end of the push member, the torque gear having a substantially cylindrical cross-sectional shape with a first protrusion extending radially out of a first side thereof.

3. The medical device of claim 2, wherein the rotation mechanism comprises a torque converter formed as a substantially cylindrical hollow element having a first longitudinal slot extending along a first side thereof, the first longitudinal slot being configured and dimensioned to engage the first protrusion.

4. The medical device of claim 3, wherein the first longitudinal slot extends in a substantially helical pattern so that axial movement of the first protrusion relative thereto causes a rotation of the torque converter.

5. The medical device of claim 3, wherein a distal end of the torque converter is coupled to the bushing.

6. The medical device of claim 3, further comprising a rotation base connected to the distal end of the flexible member, a distal portion of the rotation base being pivotally connected to the rotation mechanism.

7. The medical device of claim 6, wherein the rotation base is non-rotatably attached to the flexible member.

8. The medical device of claim 6, wherein the rotation base is rotatable relative to the torque converter.

9. The medical device of claim 6, wherein the torque gear is non-rotatably fixed to the rotation base and axially slidable relative thereto.

10. The medical device of claim 6, wherein an inner wall of the rotation base comprises a guide rib configured to mate with a guide groove provided on an outer surface of the torque gear to aid in rotational alignment of the rotation base with the torque gear.

11. The medical device of claim 1, further comprising a control wire extending through the push member.

12. The medical device of claim 1, wherein the flexible member comprises a coil.

13. The medical device of claim 1, wherein the end effector is one of a clip, biopsy device, an opening/closing instrument and an extension/retraction instrument.

14. The medical device of claim 1, wherein the flexible member is permanently affixed to the handle.

15. A hemostatic clip device, comprising
a flexible member extending from a proximal end coupled to a handle which remains outside a body accessible to a user to a distal end which, in use, is inserted into the body to a target site;
a rotation mechanism connected to the distal end of the flexible member;
a clip releasably coupled to a distal portion of the rotation mechanism via a bushing; and
a push member extending through the flexible member from a proximal portion within the handle to a distal end and connecting to the rotation mechanism, the rotation mechanism being configured and dimensioned to convert axial movement of the push member into rotation of the clip.

16. The hemostatic clip device of claim 15, further comprising a control wire extending through the device to operably control movement of the clip between a closed configuration wherein first and second arms are separated from one another by a first distance and an open configuration wherein the first and second arms are separated from one another by a second distance greater than the first distance.

17. The hemostatic clip device of claim 15, further comprising:
a torque gear connected to a distal end of the push member, the torque gear having a substantially cylindrical cross-sectional shape with a first protrusion extending radially out of a first side thereof; and
a torque converter formed as a substantially cylindrical hollow element having a first longitudinal slot extending along a first side thereof, the first longitudinal slot being configured and dimensioned to engage the first protrusion.

18. The hemostatic clip device of claim 15, further comprising:
a handle connected to the flexible member and having an opening extending therethrough to receive the push member therethrough.

* * * * *